United States Patent [19]
Zhang et al.

[11] Patent Number: 5,861,279
[45] Date of Patent: Jan. 19, 1999

[54] BACULOVIRUS EXPRESSION SYSTEM FOR HUMAN INTERLEUKIN 5 RECEPTOR AND METHOD OF SCREENING FOR INTERLEUKIN 5 ANTAGONISTS

[75] Inventors: Ji Zhang, Princeton Junction; Peng Wang, Edison, both of N.J.

[73] Assignee: Schering Corporation, Kenilworth, N.J.

[21] Appl. No.: 785,531

[22] Filed: Jan. 11, 1997

[51] Int. Cl.$^6$ ............................. C12N 15/87; C12N 15/63
[52] U.S. Cl. .................. 435/69.1; 435/348; 435/320.1; 536/23.5; 935/23; 935/57; 935/70
[58] Field of Search .................................. 435/69.1, 384, 435/320.1; 536/23.5; 935/23, 57, 70

[56] References Cited

U.S. PATENT DOCUMENTS

| | | | |
|---|---|---|---|
| 4,568,649 | 2/1986 | Bertoglio-Matte | 436/534 |
| 5,112,961 | 5/1992 | Hayashida et al. | 435/69.5 |
| 5,229,501 | 7/1993 | Keifer et al. | 530/399 |
| 5,453,491 | 9/1995 | Takatsu et al. | 530/310 |

FOREIGN PATENT DOCUMENTS 0 492 214 A2  7/1992  European Pat. Off. .

OTHER PUBLICATIONS

Blanco et al., *Proc. Natl. Acad. Sci. USA*, 90(5):1824–1828 (1993).
Cascio, *Meth. Neurosci.*, 25:175–200 (1995).
Coffman et al., *Science*, 245:308–310 (1989).
Hayashida et al., *Proc. Natl. Acad. Sci. USA*, 87:9655–9659 (1990).
Lindqvist et al., *Scandinavian J. Immunol.*, 38(3):267–272 (1993).
Luckow et al., *Bio/Technology*, 6:47–55 (1988).
Murata et al., *J. Exp. Med.*, 175:341–351 (1992).
Tavenier et al., *Cell*, 66:1175–1184 (1991).
Thompsen et al., *Bioprocess Technol.*, 17 (Insect Cell Culture Engineering):105–138 (1993).
Webb et al, *Technique* 2(4) 1990, pp. 173–188.
Gavernier et al, *PNAS* 89, 1992, pp. 7041–7045.
Leed; *Current Biotechnology* 1995, 6, pp. 567–573.

*Primary Examiner*—Garnette D. Draper
*Attorney, Agent, or Firm*—Immac J. Thampoe; Cynthia L. Foulke

[57] ABSTRACT

A baculovirus/insect cell expression system in which both α and β subunit of human IL-5 receptor can be over-expressed together in Sf9 cells has been developed. This system is able to express the human high-affinity IL-5 receptors at a very high level and finds use in a screening assay for IL-5 receptor-based antagonists. A preferred embodiment of the screening assay involves the use of peanut agglutinin as lectin in a scintillation proximity assay.

9 Claims, No Drawings

BACULOVIRUS EXPRESSION SYSTEM FOR HUMAN INTERLEUKIN 5 RECEPTOR AND METHOD OF SCREENING FOR INTERLEUKIN 5 ANTAGONISTS

This application claims the benefit of U.S. Provisional Application No. 60/010,141, filed Jan. 17, 1996.

FIELD OF THE INVENTION

The invention relates to an expression system for the human high affinity interleukin 5 receptor. More particularly, the invention is directed to a method of screening for interleukin 5 receptor-based antagonists using a baculovirus/Sf9 expression system.

BACKGROUND OF THE INVENTION

Human interleukin 5 (IL-5) is a lineage-specific cytokine released mainly from activated T cells. Sanderson, 1992, *Blood* 79:3101–3109. Takatsu et al., 1988, *Immunol. Rev.* 102:107–135. A number of studies have demonstrated that IL-5 is responsible for the differentiation, proliferation and maturation of eosinophils from their progenitors in the bone marrow. Saito et al., 1988, *Proc. Natl. Acad. Sci. USA* 85:2288–2392. Lopez et al., 1988, *J. Exp. Med.* 167:219–224. Clutterbuck and Sanderson, 1988, *Blood* 71:646–658. Clutterbuck et al., 1989, *Blood* 73:1504–1512. Ema et al., 1990, *Blood* 76:1956–1961.

IL-5, Interleukin-3 (IL-3) and granulocyte-macrophage colony-stimulating factor (GM-CSF) exhibit similar functions on eosinophils in vitro. Clutterbuck et al., 1989, *Blood* 73:1504–1512. Ema et al., 1990, *Blood* 76:1956–1961. However, whereas the action of human IL-5 is restricted to eosinophil and closely related basophil lineages (Sanderson, 1992 *Blood* 79:3101–3109), IL-3 and GM-CSF also have activities on other hematopoietic lineages. Miyajima et al., 1993, *Blood* 82:1960–1974.

IL-5 mediates its activity through a cell membrane receptor complex. This complex has been characterized physicochemically in both the murine and human systems. Mita et al., 1989, *Proc. Natl. Acad. Sci. USA.* 86:2311–2315. Plaelinck et al., 1990, *J. Exp. Med.* 172:623–691. Two receptor proteins, with molecular masses closely resembling those of murine IL-5 receptor α- and β-chains (mIL-5Rα and mIL-5Rβ) are involved in the binding of human IL-5 (hIL-5). The α-chain (60 kd component) corresponds to the low affinity IL-5 binding site ($K_d=10^{-9}M$). The β-chain (130 kd component) associates with the α-chain to form the high affinity binding site ($K_d=2.5\times10^{-10}M$). Tavernier et al., 1991, *Cell* 66:1175–1184. Miyajima et al., 1993, *Blood* 82:1960–1974. High affinity human IL-5 receptors (hIL-5R) have been found in eosinophils and their related cell lines. Migita et al., 1991, *Cell. Immunol.* 133:484–497; Ingley and Young, 1991, *Blood* 78:339–344.

The cDNAs encoding the human α-chain component (hIL-5Rα) and the human β-chain component (hIL-5β) have been cloned and characterized. Tavernier et al., 1991, *Cell*, 66:1175–1184. Murata et al., 1992, *J. Exp. Med.* 175:341–351. Hayashida et al., 1990, *Proc. Natl. Acad. Sci. USA* 87:9655–9659. The α subunit is responsible for IL-5 binding specificity and is distinct from the IL-3Rα subunit and the GM-CSFRα subunit. Consistent with the studies of receptor binding assays, Northern blot experiments also have demonstrated that the expression of IL-5Rα mRNA is restricted to eosinophils and their related cell lines. The β subunit is shared by IL-3R and GM-CSFR and is essential for both the formation of high-affinity receptor complexes and signal transduction. Miyajima et al., 1993, *Blood* 82:1960–1974. Nucleotide sequencing and binding experiments show that the β receptor component is identical to the β-chain component of human GM-CSFR. Tavernier et al., 1991, *Cell* 66:1175–1184. Takaki et al, 1993, *J. Exp. Med.* 177:1523–1529. The cell type specific expression of the IL-5Rα chain appears to be a required and crucial factor for the specific roles of IL-5 to these cells. Miyajima et al., 1993, *Blood* 82:1960–1974.

The process of eosinophilopoiesis is increased in certain disease states. Eosinophilia is characteristic of most parasitic infections as well as other disorders including dermatoses, allergies, polyarteritis nodosa and neoplastic diseases. Bronchial eosinophilia is a cardinal feature of chronic asthma. Multiple lines of evidence indicate that overexpression of IL-5 plays a crucial role in a number of eosinophil-related diseases. Owen et al., 1989, *J. Exp. Med.* 170:343–348. Owen et al., 1990, *Proc. Natl. Acad. Sci. USA* 87:8647–8651.

A central and specific role of IL-5 in controlling eosinophil functions in vivo was suggested by studies that mice bearing an IL-5 transgene produce a specific eosinophilia. Vaux et al., 1990, *Int. Immunol.* 2:965–970. Dent et al., 1990, *J. Exp. Med.* 172:1425–1431. Limaye et al., 1990, *J. Exp. Med.* 172:399–402. Moreover, antibodies specific to IL-5 inhibit eosinophil production induced by parasites and pathological stimuli. Coffman et al., 1989, *Science* 245:308–310. Gulbenkian et al., 1992, *Am. Rev. Respir. Dis.* 146:263–265. Ohnishi et al., 1993, *Am. Rev. Respir. Dis.* 147:901–907. A selective enhancement of IL-5 production was demonstrated in human helminth-infected patients with eosinophilia and in eosinophilic mice infected with *Toxocara canis*. Limaye et al., 1990, *J. Exp. Med.* 172:399–402 and Yamaguchi et al. 1990, *Exp. Hematol.* 18:1152–1157, respectively.

There is a need in the art to find therapeutic compounds useful in the treatment of chronic asthma and other IL-5-based disorders and disease states with demonstrated eosinophilia. There thus is a need for an expression system capable of expressing high affinity IL-5R at high levels and methods that can be used to identify receptor-based IL-5 antagonists potentially useful as therapeutic agents.

SUMMARY OF THE INVENTION

The present method fulfills this need by providing an expression system capable of expressing high levels of high affinity human interleukin 5 receptor and methods for screening for interleukin 5 antagonists.

The invention provides a recombinant baculovirus comprising DNA encoding human interleukin 5 receptor α-chain and/or DNA encoding human interleukin 5 receptor β-chain, which virus is capable of expressing such DNA in a host cell.

The invention also provides a host cell comprising at least one recombinant baculovirus, which host cell is capable of coexpressing DNA encoding human interleukin 5 receptor α-chain and human interleukin 5 receptor β-chain.

The invention further provides a method for producing a cell, the membrane of which contains high levels of high affinity human interleukin 5 receptors comprising:

(a) infecting host cells with at least one recombinant baculovirus, said baculovirus containing DNA encoding human interleukin 5 receptor α-chain, DNA encoding human interleukin 5 receptor β-chain, or DNA encoding both human interleukin 5 receptor α-chain and human interleukin 5 receptor β-chain, to produce an infected host cell capable of coexpressing said DNA encoding human interleukin 5 receptor α-chain and human interleukin 5 receptor β-chain, and (b) maintaining the infected host cells under conditions permitting the coexpression of said DNA encoding human interleukin 5 receptor α-chain and human interleukin 5 receptor β-chain.

Still further, the invention provides a method for identifying interleukin 5 antagonists using an interleukin 5 receptor binding assay comprising:

(a) contacting baculovirus infected host cells expressing high affinity human interleukin 5 receptors with a sample suspected to contain an interleukin 5 antagonist in the presence of a predetermined amount of labeled interleukin 5; and (b) measuring the amount of labeled interleukin 5 bound specifically to the cells;

whereby the presence of an interleukin 5 antagonist in the sample will be indicated by measurement of a substantially reduced amount of labeled interleukin 5 bound specifically to the cells compared to the amount measured using a control sample.

A preferred embodiment of the invention is directed to a method of detecting interleukin 5 antagonists through the use of a scintillation proximity assay (SPA). Most preferably, the method comprises:

(a) mixing intact baculovirus infected insect cells expressing membrane bound human high affinity interleukin 5 receptor, biotin-labeled peanut agglutinin, streptavidin-SPA beads, labeled interleukin 5, and a sample suspected to contain an interleukin 5 antagonist; and (b) measuring the amount of labeled interleukin 5 bound specifically to the cells;

whereby the presence of an interleukin 5 antagonist in the sample will be indicated by measurement of a substantially reduced amount of labeled interleukin 5 bound specifically to the cells compared to the amount measured using a control sample.

DETAILED DESCRIPTION OF THE INVENTION

All references cited herein are incorporated in their entirety by reference.

The invention is directed to a baculovirus expression system which finds use in a receptor-based IL-5 antagonist screening assay. It has been discovered that high levels of high affinity hIL-5R can be expressed in insect cells infected with at least one recombinant baculovirus comprising DNA encoding the human IL-5Rα-chain and/or human IL-5Rβ-chain. The invention is based on the discovery that functional membrane-bound hIL-5Rα and β can be coexpressed as high affinity hIL-5R in insect cells, which cells can then be advantageously used in an assay to screen for compounds which inhibit binding of IL-5 to the IL-5 receptors.

The nucleotide and amino acid sequences of hIL-5Rα and hIL-5Rβ are known in the art. The nucleotide and amino acid sequences of the hIL-5Rα-chain are disclosed, for example, in EP 0 475 746, EP 0 492 214, Tavernier et al., 1991, *Cell,* 66:1175–1184, and Murata et al., 1992, *J. Exp. Med.* 175:341–351. The nucleotide and amino acid sequences of the hIL-5Rβ-chain are disclosed, for example, in Hayashida et al., 1990, *Proc. Natl. Acad. Sci. USA* 87:9655–9659.

DNA constructs encoding hIL-5Rα and/or hIL-5Rβ may be of genomic or cDNA origin; for instance, they can be obtained by preparing a genomic or cDNA library and screening for DNA sequences coding for all or part of the α or β chain by hybridization using synthetic oligonucleotide probes and standard techniques. Sambrook et al., Molecular Cloning: A Laboratory Manual, 2nd Edition, Cold Spring Harbor, 1989. The DNA constructs encoding hIL-5Rα and/or hIL-5Rβ may also be prepared synthetically by established standard methods, e.g., in an automatic DNA synthesizer, and then purified, annealed, ligated and cloned in suitable vectors. In addition, the DNA constructs may be of mixed synthetic and genomic, mixed synthetic and cDNA or mixed genomic and cDNA origin prepared by ligating fragments of synthetic, genomic or cDNA, the fragments corresponding to various parts of the entire DNA construct, in accordance with standard techniques. The DNA constructs may also be prepared by polymerase chain reaction using specific primers. All of these techniques are well within the skill of the art.

Such DNA constructs may contain the entire native sequence of hIL-5Rα and/or β or a homologue thereof. The term "homologue" is intended to indicate a natural variant of the DNA sequence encoding human IL-5Rα and/or β or a variant produced by modification of the DNA sequence. Examples of suitable modifications of the DNA sequence are nucleotide substitutions which do not give rise to another amino acid sequence of the hILR-5β or β or nucleotide substitutions which do give rise to a different amino acid sequence and therefore, possibly, a different protein structure. Other examples of possible modifications are insertions of one or several nucleotides into the sequence, addition of one or several nucleotides at either end of the sequence, or deletion of one or several nucleotides at either end or within the sequence. Any homologous DNA sequence encoding a protein which exhibits hIL-5R activity (e.g., with respect to IL-5 binding specificity) similar to that of the naive protein is contemplated for use in the claimed invention.

It will be appreciated by those skilled in the art that the cloned human IL-5Rα and β cDNAs may be recombinantly expressed by molecular cloning into an expression vector containing a suitable promoter and other appropriate transcription regulatory elements, and transferred into a host cell to produce recombinant hIL-5Rα and β. The procedures used to ligate the DNA sequences of interest, the promoter and the terminator, respectively, and to insert them into suitable vectors containing the information necessary for replication are well known to persons skilled in this art. Expression vectors are defined herein as DNA sequences required for the transcription of cloned copies of genes and the translation of their mRNAs in an appropriate host. Expression vectors contemplated for use in the practice of the invention are recombinant baculoviruses.

*Autographa californica* nuclear polyhedrosis virus (AcMNPV), the prototype virus of the family Basculovirudae, has a wide host range and infects more that 30 species of Lepidotpteran insects. Its genome consists of double-stranded, circular, super-coiled DNA approximately 128 kilobases in length. Smith and Summers, 1978, *Virology,* 89:517–527. Smith and Summers, 1978, *J. Virol.* 30:828–838. Helper-independent baculovirus expression vectors have been used for the expression of a wide variety of heterologous genes. Smith et al., 1983, *J. Virol.* 46:584–593. Smith et al., 1983, *Mol. Cell. Biol.* 3:2156–2165. Such vectors are known in the art and are commercially available.

The recombinant baculovirus utilizes the highly expressed and regulated AcMNPV polyhedrin promoter to control the inserted foreign genes. This allows expression of prokaryotic or eukaryotic genes to produce fused or nonfused recombinant proteins. An intermediate plasmid construct, designated as a baculovirus transfer vector, is used to insert the gene(s) of interest into the baculovirus genome at a specific region. Such transfer vectors will usually contain sequences from AcMNPV including the promoter of the polyhedrin gene and varying amounts of 5' and 3' viral DNA flanking the polyhedrin gene cloned into a high copy number bacterial plasmid. The desired foreign gene sequences in the recombinant plasmid can be transferred to wild-type AcMNPV by homologous recombination within a cell transfected with both the plasmid and wild-type virus DNAs. An overview of the baculovirus expression system and the methods used therein may be found in Luckow and Summers, 1988, *Bio/Technology* 6:47–55 and Luckow and Summers, 1988, "A Manual of Methods for Baculovirus Vectors and Insect Cell Culture Procedures", Texas Agricultural Experimental Station, Texas A&M University, Bulletin No. 12555, 2nd edition.

Despite its powerful and versatile characteristics, the baculovirus expression systems were, heretofore, only widely used for producing the soluble, secreted and single polypeptide-containing proteins. Expression of a membrane-bound protein with multiple subunits, such as human high affinity IL-5 receptor, has not heretofore been accomplished using a baculovirus/insect system.

The host cell into which the recombinant baculovirus is introduced is an insect cell, in particular Lepidotpteran insect cells, preferably *Spodoptera frugiperda* cells, more preferably an Sf9 cell line. While expression in Sf9 cells is described in detail below, one skilled in the art would recognize that other insect host cells may advantageously be used in the practice of the invention.

High affinity IL-5R is expressed by infecting insect cells with a recombinant baculovirus containing DNA encoding both hIL-5Rα-chain and hIL-5Rβ-chain. Alternatively, insect cells can be infected with a first recombinant baculovirus containing DNA encoding hIL-5Rα-chain and a second recombinant baculovirus containing DNA encoding hIL-5Rβ-chain. The infected host cells are then cultured in a suitable nutrient medium under conditions which are conductive to the expression of both the α and β DNA sequences. The medium used to culture the cells may be any conventional medium suitable for growing the insect cell line. Suitable media are available from commercial suppliers (e.g., medium Sf-900 II SFM available from GIBCOBRL, Cat. No. 10902-088) or may be prepared according to published recipes.

A major advantage of this invertebrate virus expression system over bacterial and yeast is the very abundant expression of recombinant proteins, which are in many cases antigenically, immunogenically, and functionally similar to their authentic counterparts. In addition, baculoviruses are not pathogenic to vertebrates or plants and do not employ transformed cells or transforming elements as do the mammalian expression systems. The baculovirus vector also utilizes many of the protein modification processing and transport systems that occur in higher eukaryotic cells and may be essential for the complete biological function of a recombinant protein.

It has been unexpectedly discovered that insect cells expressing high levels of high affinity hIL-5R can be prepared by infecting insect cells with at least one baculovirus containing DNA encoding hIL-5Rα-chain and/or DNA encoding hIL-5Rβ-chain. While the assay of the invention can be used with isolated membranes expressing high affinity hIL-5R, the binding assay of the invention is preferably performed using intact cells, in particular intact SF9 cells co-expressing both the α and β subunits of the high affinity human IL-5 receptor. It has been surprisingly discovered that insect cells expressing high affinity hIL-5R may be use in the intact state in IL-5 receptor binding assays. The use of intact cells in assays for IL-5 antagonists more closely parallels the relevant physiological condition. Moreover, there is no need to break up the cells and recover the membrane component from the cellular debris, thus saving costly and time-consuming processing steps. In addition, large quantities of insect cells expressing high affinity hIL5R can be prepared and stored in the frozen state until needed for use in the method of the invention.

Generally, in receptor binding assays used to screen for IL-5 antagonists, putative IL-5 antagonists are combined with labeled IL-5 and binding of the IL-5 to the cell is measured. Potential IL-5 antagonists are defined as molecules capable of binding to the IL-5 receptor or to IL-5, thus reducing or inhibiting binding of IL-5 to the receptor. Antagonists identified in accordance with the invention are selected for further study.

In a preferred embodiment, a scintillation proximity assay (SPA) is used to screen for IL-5 antagonists. Scintillation proximity assays of the type contemplated for use in the practice of the invention are described in U.S. Pat. No. 4,568,649. Generally, SPA uses a plurality of beads or other types of support structure that are impregnated and/or coated with a scintillator or fluorescer (i.e., a material capable of excitation or fluorescence when excited by radioactive energy, such as diphenyloxazole, DPO). Various types of beads may be utilized, such as polyacrylamide, acrylamide, agarose, polystyrene, polypropylene, polycarbonate or Sepharose 4B beads (Pharmacia Fine Chemicals, Uppsala, Sweden). Other shapes or types of support structures, for instance latex particles, may be used as long as ligand molecules can be covalently or otherwise attached thereto and a fluorescer integrated therewith.

The beads are coated with a ligand that is capable of specifically binding to a reactant of interest by covalently linking or directly attaching the ligand to the beads. The beads are then mixed in a water-based solution containing the reactant that has been radiolabeled. Upon binding of the radiolabeled reactant to the ligand, the fluorescer integrated into the bead is placed in close enough physical relationship to the reactant to allow the radiation energy emitted from the reactant to activate the fluorescer thereby causing the fluorescer to emit light energy. The level of light energy emitted may be conveniently measured with a scintillation counter or other monitoring device employing a photomultiplier tube. Since the radiolabeled reactant that does not bind to the ligand is, for the most part, disposed too far away from the beads to enable the radioactive energy emitted thereby to reach the fluorescer integrated into the beads, the level of light energy produced by the fluorescer is indicative of the amount of reactant bound to the beads. Since the reactant that has not bound to the ligand is too far away from the support beads to permit the radiation energy emitted there from reaching the fluourescer, the radioactive reactant that has not bound to the ligand need not be separated from the ligand-reactant complex prior to measuring the level of light energy emitted by the fluorescer. Use of the SPA thus involves fewer manipulations and eliminates the time-consuming procedure of separation of the unbound labeled reactant from the bound complexes by centrifuge, precipitation, washing and other procedures. In addition the large quantities of radioactive waste material produced by these separation techniques is also avoided.

In the practice of the invention radiolabeled hIL-5 is used as the labeled reactant. The radiolabeled IL-5 is biologically and chemically identical to unlabeled IL-5, with the exception that the labeled reactants emit radioactive energy due to the decaying of the radioactive isotope present. The technique used for labeling of the reactant varies with the type of radioactive isotope employed. For instance, labeling can be accomplished by replacing one of the atoms of the reactant molecules with a corresponding radioactive isotope. A hydrogen atom could be replaced with tritium, $^3$H; a carbon atom replaced with carbon-14, $^{14}$C; or a strontium atom replaced with strontium-38, $^{38}$Sr. In another labeling process, rather than replacing the atoms of the reactant with a radioactive isotope, an isotope may be added to the reactant molecule. Such radioactive isotopes in common use include iodine-125, $^{125}$I; and iron-59, $^{59}$Fe. Methods of radiolabeling reactants is well within the skill of the art.

In a preferred embodiment of the invention, intact Sf9 cells expressing high affinity hIL-5R are coupled to streptavidin-coated SPA beads using biotin-labeled peanut agglutinin (PNA). Radiolabeled IL-5 and the sample to be tested (e.g., for IL-5 antagonist activity or for the presence of IL-5) are added and binding of the radiolabeled reactant to the cells measured. Both direct and competitive assays are contemplated for use.

Direct assays are preferred when the assay is used to screen for IL-5 antagonists. If an antagonist is present, less light is emitted. A competitive assay may advantageously be used to quantitatively determine the amount of IL-5 present in a sample. The non-labeled IL-5 in the sample competes with the labeled IL-5 for the receptors. The more IL-5 present in the sample, the less light is emitted.

It is a surprisingly discovery of the invention that the use of PNA as a binding component results in a high signal-to-noise ratio. Using PNA, high signal-to-noise ratios (20- to 30-fold) can be obtained, compared to 5- to 6-fold ratios obtained with conventionally used lectins such as wheat germ agglutinin (WGA) and concanavalin A (Con A).

The IL-5 receptor binding SPA can advantageously be performed in 96-well plates. Dimethyl sulfoxide (DMSO) concentrations up to 4% can be used. For the high throughput screening, test compounds are preferably dissolved in DMSO. In the scintillation proximity screening assay using PNA in accordance with the invention, the SPA has been unexpectedly found to be at least as sensitive as the filtration format receptor binding technique. Binding is specific for IL-5, and inhabitable by unlabeled IL-5 in a dose dependent manner.

The invention will be discussed in more detail by way of the following examples.

EXAMPLE 1

Construction of a Recombinant Baculovirus
Transfer Vector Containing a DNA Insert Encoding
hIL-5Rα (p2BacIL5Rα)

Based on the human IL-5Rα-chain sequence disclosed in Murata et al. (*J. Exp. Med.* (1992) 175:341–351), specific primers were designed and PCR used to amplify IL-5Rα cDNA from the mRNA of TF-1 cells, an erythroleukemic cell line. A vector, pSRS (ATCC 68234) was used to clone IL-5α cDNA. The final plasmid, which contained the human IL-5 receptor α chain cDNA insert (1.3 kb), was named pSRG5RFL. p2Bac (7.1 kb), obtained from Invitrogen (Cat. No. V1980-10), served as a backbone for the recombinant baculovirus transfer vector of the invention. Using standard DNA manipulation protocols, p2Bac and pSRG5RFL were used to construct a transfer vector containing a DNA sequence encoding hIL-5Rα (p2BacIL5Rα).

Both p2Bac and pSRG5RFL plasmids were initially digested, respectively, with a restriction enzyme EcoRI (Promega) under conditions suggested by the manufacturer. The 1.3 kb cDNA insert of human IL-5 receptor α-chain was isolated from the EcoRI digested pSRG5RFL after a gel-electrophoresis separation. This cDNA insert was then ligated into the EcoRI digested p2Bac vector with a ligation kit (Cat. No. 203003, Stratagene) in accordance with the manufacturer's instructions. The ligated DNA was then transformed into competent *E. coli* cells (MAX Efficiency DH5a™ Competent Cells, Cat. No. 18258-012, GIBCOBRL) with a procedure provided by the manufacturer. The individual colonies were picked up from the plate containing the transformed bacterial cells and cultured in 5 ml of the liquid medium. The plasmids were isolated and purified from the bacterial cell with INSTA-MINI-PREP™ Kit (Cat. No. p1-123456, 5 Prime-3 Prime, Inc.) and screened with XbaI digestions for the presence of the cDNA inserts and its orientation. After XbaI digestion, the plasmids that contains the 1.3 kb cDNA insert with the correct orientation gave rise to the both 7.7 kb and 0.69 kb DNA fragments illustrated on gel electrophoresis analysis. The resultant plasmid containing the 1.3 kb cDNA insert with the correct orientation was then digested with a restriction enzyme, NcoI (Cat. No. 15421-019, GIBCOBRL) under conditions specified by the manufacturer. Next, the NcoI digested DNA was treated with mung bean nuclease (Cat. No. 18041-012, GIBCOBRL) under conditions suggested by the manufacturer to remove the single-stranded termini. The purpose of this step was to remove a ATG (start codon) sequence that was localized at the immediate upstream region of the 1.3 cDNA insert. Therefore, the expression of the cDNA encoding protein will not be interfered by this start codon, ATG, in the final expression system. Following the mung bean nuclease treatment, the blunt-end linearized plasmid DNA was religated with the same ligation kit as described above and then transformed into the *E. coli* cells with the same commercially available competent cells as described above. The individual bacterial colonies were picked up and cultured as described above. The plasmids were extracted with the same kit and procedure as describe above and then screened with NcoI digestion. The plasmid that was not cut by NcoI was the final plasmid and was designated p2BacIL5Rα.

Construction of a Recombinant Baculovirus
Transfer Vector Containing a DNA Insert Encoding
hIL-5Rβ (p2BacIL5Rβ)

p2Bac was also used as a host vector to clone the cDNA insert of human IL-5 receptor β-chain. The 3.0 kb cDNA insert of human IL-5 receptor β-chain was obtained from pKH97, prepared as described in Hayashida et al., (*Proc. Natl. Acad. Sci.*, (1990) 87:9655–9659). The basic procedures and the kit used for DNA manipulations, transformations and bacterial cultures used to prepare p2BacIL5Rβ were identical to those used for the construction of p2BacIL5Rα described above.

First, p2Bac was digested with the two restriction enzymes, XbaI and SmaI (Promega) and the digested 7.1 kb fragment was then purified from the gel with the GENECLEAN II kit (Bio 101 Inc.) after the gel electrophoresis of the digested p2Bac. At the same time, pKH97 was subject to the digestion of restriction enzyme, XhoI (Promega), followed by blunting the end with the klenow fill-in kit (Cat. No. 200410, Stratagene) and its protocol. Then the XhoI digested pKH97 was further digested with two restriction enzyme XbaI and HindIII. Next, the 3.0 kb XhoI/XbaI digested fragment (human IL-5 receptor β cDNA) was purified from the gel with GENECLEAN II kit after the gel electrophoresis of the digested pKH97. Finally, The 7.1 kb XbaI/SmaI digested p2Bac and 3.0 kb XhoI/XbaI cDNA insert were mixed together and subject to ligation reaction with a ligation kit followed by transforming the ligated DNA into *E. coli* cells. The plasmids were purified from the mini-scale bacterial cultures and screened with restriction digestion using the enzymes XbaI and Bg1II. The plasmid that produced three fragments with the sizes of about 6.7, 2.1 and 1.28, separately, after XbaI/Bg1II digestion was retained and designated p2BacIL5Rβ. This plasmid contains the cDNA insert of human IL-5 receptor β-chain with the correct orientation.

Construction of a Recombinant Baculovirus Transfer Vector Containing DNA Inserts Encoding hIL-5Rα and hIL-5Rβ (p2BacIL5Rαβ)

The DNA manipulation procedures and reagent kits are identical to those described above. First, p2BacIL5Rα was digested with the restriction enzymes BamHI and HindIII (Promega) and the BamHI/HindIII digested 1.3 kb cDNA insert of hIL-5Rα was isolated from gel after the gel electrophoresis. At the same time, p2BacIL5Rβ was also subject to the restriction digestions of BamHI and HindIII and then the 10.3 kb digested fragment of hIL-5Rβ was isolated from the gel after gel electrophoresis. Subsequently, the 1.3 kb cDNA insert was ligated with the 10.3 kb fragment in a DNA ligation reaction. The ligated DNA was then transformed into *E. coli* cells. The plasmids were purified from the mini-cultured bacterial cells and screened, separately, with either XbaI or EcoRI digestions. The plasmid containing both the α and β cDNA inserts with the correct orientations produced two XbaI digested fragments of 8.0 kb and 3.6 kb sizes, and generated two EcoRI digested fragments of 10.3 kb and 1.3 kb sizes. One of these plasmids was retained and designated p2BacIL5Rαβ.

Generation of the Recombinant Baculoviruses

The baculovirus transfer vector, p2BacIL5Rαβ, was used to generate the recombinant baculovirus containing both the α and β cDNA inserts. Two recombinant baculoviruses containing either the α cDNA insert or β cDNA insert were also generated following similar procedures by using transfer vectors p2BacIL5Rα and p2BacIL5Rβ, respectively.

The recombinant baculoviruses were generated by co-transfection of the wild type baculovirus (AcMNPV) DNA with the transfer vector p2BacIL5Rαβ. The presence of the cDNA insert at the locus of the polyhedrin gene of the AcMNPV baculoviral DNA in the recombinant baculoviruses were verified by PCR analysis using a pair of primers specific to the sequences of the polyhedrin gene: Forward primer (−44) 5'-TTTA CTGT TTTC GTAA CAGT TTTG-3'; and Reverse primer (+778) 5'-CAAC AACG CACA GAAT CTAG-3' (SEQ ID NOS 1 and 2, respectively). Based on the distance between the two primers (734 bp) and the size of the α cDNA insert (1.3 kb), the recombinant baculoviral DNAs with the cDNA insert(s) generates a specific PCR product with the size of 2,034 kb using this pair of primers.

Viral DNAs of clones (designated as clones 2, 3 and 4) gave the specific DNA fragments, generated by PCR, suggesting that these viral clones were recombinant viruses containing at least the IL-5Rα cDNA insert. These clones were therefore amplified for further characterization. The PCR characterization of the recombinant viral genomes were performed by the custom baculovirus service group, Invitrogen Corporation. The PCR condition was as follows: 1 cycle of 2 minutes at 94° C.; 30 cycles of 1 minutes at 94° C., 2 minutes at 55° C. and 3 minutes at 72° C.; 1 cycle of 7 minutes at 72° C.

Characterization of the Recombinant Baculoviruses

Sf9 cells were seeded at $0.5 \times 10^6$ cells/ml and cultured at 27° C. for 3 days in medium Sf-900 II SFM (GIBCOBRL, Cat. No. 10902-088) supplemented with 2 mM glutamine and 3% fetal bovine serum. The cells, at the concentration of $2 \times 10^6$ cells/ml, were infected with the recombinant viral clones 2, 3 and 4, separately. After the two-day infections, the cells were harvested and the total RNAs were extracted from the infected cells with TRISOLV™ RNA isolation kit (BIOTECX LABORATORIES, INC.) in accordance with the manufacture's instructions. The total RNAs were subject to RT-PCR analysis using GeneAmp RNA kit (Perkin Elmer Cetus, Cat. No. N808-0017) following the manufacture's instructions.

First, 0.5 µg total RNAs were transcribed into the cDNA with the reverse transcriptase. The PCR reactions were then carried out with the above cDNAs and the gene specific primers. The primers for human IL-5 receptor α cDNA were: Forward primer (+499): 5'-AAGC AAAT GTGT AACC ATCC TCCA CAAA GG-3'; and Reverse primer (+1060): 5'-AAAG CAAT GGAT TGGA AAAG CAGA CACT GG-3' (Clontech, Cat. No. 9203-1) (SEQ ID NOS 3 and 4, respectively). Therefore, the 561-bp DNA fragments was used to show the correct PCR products specific to the mRNA of the α cDNA. The primers for human IL-5 receptor β cDNA were: Forward primer (+1180): 5'-AAGG ACAG CAAG ACCG AGAC C-3'; and Reverse primer (+1930): 5'-CCCC CAGC AGGC AGAC ACAG G-3' (SEQ ID NOS 5 and 6, respectively). Using this pair of primers, the appearance of 750-bp DNA fragments on the gel indicate the specific PCR products for the mRNA of the β cDNA.

Sf9 cells infected with viral clones 2 and 3 expressed both the α and β mRNA of human IL-5 receptor, based on the appearances of the specific PCR products described above. In contrast, the cells infected with viral clone 4 expressed only the α-chain specific mRNA but not the β chain specific mRNA. Therefore, viral clones 2 and 3, which contain both the α and β cDNA inserts, are the desired recombinant baculoviruses.

Sf9 cells infected with recombinant viral clone 2 was further characterized. RT-PCR analysis indicated that Sf9 cells infected with the recombinant viral clone 2 expressed the mRNAs specific to both the α and β cDNA inserts. Western blot experiments were performed using antibodies specific to both the α and β proteins of hIL-5R to determine the protein expressions and their apparent sizes on SDS-PAGE gel. The cells infected with clone 2 were harvested after one day infection and then lysed in SDS-gel loading buffer (62.5 mM Tris•HCl, pH 6.8/1% SDS/0.0025% bromphenol blue/2.5% 2-mercaptoethanol/10% glycerol) containing 5M urea. Equal amounts of cell extracts were loaded on the gel and the proteins were resolved by electrophoresis on 8–16% polyacrylamide/SDS minigels (Novex, San Diego). Then the proteins on the gel were electrophoretically transferred to nitrocellulose membranes. The membranes were blocked by overnight incubation at 4° C. in PBS/5% dry milk/0.1% Tween-20.

For detecting the α chain protein, a polyclonal rabbit IgG specific for the α chain of human IL-5 receptor was prepared using methods known in the art and used at 1:2500 dilution following a pre-incubation with non-infected Sf9 cell lysates for 1 hour. The membranes were incubated for 1 hour at room temperature in 10 ml of PBS/1% fetal bovine serum/0.1% Tween-20/ 4 µl anti-α antibody. The membranes were then incubated with a second antibody, HPR-labeled anti rabbit IgG (Amersham), at a 1:4000 dilution in 10 ml of PBS/0.1% Tween-20 for 1 hour after several washings. The antibody was developed with ECL western blotting analysis system (Cat. No. RPN 2108; Amersham) and its protocols.

For detecting the β chain of human IL-5 receptor, a mouse monoclonal IgG (0.1 mg/ml) specifically against the β chain protein was purchased from Santa Cruz Biotechnology, Inc (Cat. No. sc-457) was used in this study at a 1:400 dilution. The remaining procedures for the β chain are similar to those used to detect the a chain except that the second antibody was HRP-labeled anti mouse IgG (Amersham) and used at a 1:2000 dilution.

The presence of both the overexpressed α and β chains of human IL-5 receptor were shown in the Sf9 cells infected with the recombinant virus clone 2 by western blot analysis using both the α and β chain-specific antibodies. The apparent sizes for both the α and β chain in this assay were about 60 kDa and 130 kDa, respectively. These results are in agreement with those reported in literature, confirming that the full-length and mature α and β chain proteins were co-expressed well in Sf9 cells infected by the recombinant baculovirus of the invention.

Sf9 cells were also infected with the same viral clone and infected cells harvested at several different time points to reveal the kinetic profiles of both the α and β chain expressions. It was found that the expression levels of the 60 kd α chain protein increased dramatically during the first two days of infection and then reached a steady-state level. In contrast, the profile of the β chain was very different. First, the expression of the full-length and mature 130 kDa protein took place and reached the peak on day two. Then the amount of 130 kDa protein began to decrease on day three and disappeared by day four. Meanwhile, two proteins with the smaller sizes were detected by the β-specific antibody on day two and their amounts were increased over the times of the infections. Based on their specific interaction with the β-chain specific antibody and appearance profile, the two smaller proteins appeared to be degraded products of the 130 kDa protein. Based on these results, a two-day infection appears sufficient for this baculovirus/insect cell system to express both intact and high-level human IL-5 receptors.

Characterization of High Affinity hIL-5 R Expressed on the Surface of Sf9 Cells Infected with the Recombinant Baculovirus The infected cells harvested in the time-course study described above were also used to perform receptor binding assays using $^{125}$I-labeled human IL-5. The cells were counted and harvested at several different time points. The data of receptor binding, $K_d$ value and binding sites/per cell were obtained with a filtration method. Table 1 shows the $K_d$ values and the binding sites per cell.

TABLE 1

| Parameters | First day | Second day | Third day |
|---|---|---|---|
| $K_d$ (pM) | 340 | 490 | 465 |
| Binding sites/cell | 92,000 | 244,000 | 327,000 |

Together, these results suggest that following its infection the recombinant baculovirus of the invention is able to express human high-affinity IL-5 receptor at a very high level in Sf9 cells.

Preparation of High-Titer Viral Stock

Recombinant viral clone 2 was used to prepare a high-titer viral stock for large-scale protein expressions. High-titer viral stocks were prepared by as follows: $2\times10^6$ Sf9 cells were seeded in two T-25 tissue culture flasks in a total of 5 ml of media. 20 µl of the original viral stock were added to the flasks. Infection was allowed to proceed for 7–10 days, at which time the entire contents of the flasks were harvested. These were then used to infect 500 ml of Sf9 cells, which were at a density of 1.8 to $2.2\times10^6$ cells/ml, and have a viability of greater than or equal to 98%. Infection was allowed to proceed 7–10 days. The high titer stock was harvested when the cell lysis was greater than or equal to 90% as determined by trypan blue dye exclusion. The cell debris was pelleted and discarded, while the supernatant was removed and stored at 4° C. The high titer stock was titered by a standard plaque assay procedure. The dilution used to titer the stock were $1:10^6$ and $1:10^7$.

Large-Scale Expression of High Affinity hIL-5R in Sf9 Cells

Sf9 cells were cultured at 27° C. in 1 liter of the medium Sf-900 II SFM (GIBCOBRL, Cat. No. 10902-088) supplemented with 2 mM glutamine and 3% fetal bovine serum until the cell density was $2.0\times10^6$ cells/ml and viability was at least 98%. Then the cells were precipitated down and resuspended in 1 liter of the fresh medium. The expressions were carried out by the infection of Sf9 cells with the high titer stock of the recombinant viral clone 2 at a MOI (Multiplicity of infection) of 5. After two days, the infected Sf9 cells were harvested and characterized by IL-5 receptor binding assays.

In another protocol, the Sf9 cells were cultured in their specific condition and 1 liter Sf9 cells with the density of $4\times10^6$ cells/ml were infected with the high titer stock of the recombinant viral clone 2 at an MOI of 2 for two days. The infected cells were harvested and characterized by IL-5 receptor binding assays. The expressions of human IL-5 receptors by each of these protocols were very similar regarding the binding affinity and receptor number per cell.

These infected Sf9 cells were collected and used in screening assays, as described in Example 2.

EXAMPLE 2

The assay is performed in 96-well microtiter plates. Assay mixtures, in a total volume of 200 µl, were prepared which contained 30,000 cells, 100,000 cpm of [$^{125}$I]IL-5, 0.125 mg of streptavidin-SPA beads, 0.6 µg of biotin-PNA, the compound to be tested or unlabeled IL-5 at various concentrations (as positive control for inhibition of the binding), in a buffer consisting of 50 mM Tris-HCl, pH 7.4, 2 mM EGTA, 3 mM MgCl$_2$, 1 mM Pefabloc SC, 10 µg/ml leupeptin, 2 µg/ml aprotinin, 0.12M NaCl, 0.1% BSA, 0.01% NaN3 and 0.75% gelatin.

The cells are first incubated with unlabeled IL-5 or the test compound at room temperature for 15 minutes with shaking, followed by addition of [$^{125}$I]IL-5. After incubation at room temperature for 10 minutes with shaking, the SPA beads mixed with biotin-PNA is added. The mixture is incubated at room temperature for 18–24 hours with shaking, then the radioactivity is directly counted in a β-counter. Under these conditions, total IL-5 binding (in the absence of unlabeled IL-5 or other binding inhibitors) is about 2000–3500 cpm, and non-specific binding (in the presence of 500-fold unlabeled IL-5) is 110–120 cpm. The binding is specific for IL-5, and inhibitable by unlabeled IL-5 in a dose dependent manner with an $IC_{50}$ of about 200 pM.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

---

We claim:

1. An insect host cell coexpressing human interleukin 5 receptor α-chain and human interleukin 5 receptor β-chain, said cell being infected with: (a) a recombinant baculovirus comprising DNA encoding human interleukin 5 receptor α-chain and a second recombinant baculovirus comprising DNA encoding human interleukin 5 receptor β-chain; or (b) a recombinant baculovirus comprising DNA encoding both human interleukin 5 receptor α-chain and human interleukin 5 receptor β-chain.

2. The host cell of claim 1 wherein said insect cell is an Sf9 insect cell line.

3. The host cell of claim 1 wherein said host cell is infected with a recombinant baculovirus comprising DNA encoding both human interleukin 5 receptor α-chain and DNA encoding human interleukin 5 receptor β-chain.

4. The host cell of claim 2 wherein said host cell is infected with a first recombinant baculovirus comprising DNA encoding human interleukin 5 receptor α-chain and a second recombinant baculovirus comprising DNA encoding human interleukin 5 receptor β-chain.

5. A recombinant baculovirus comprising DNA encoding human interleukin 5 receptor α-chain and DNA encoding human interleukin 5 receptor β-chain, which virus is capable of coexpressing human interleukin 5 receptor α-chain and human interleukin 5 receptor β-chain in a host cell.

6. A method for producing a cell, the membrane of which contains high levels of high affinity human interleukin 5 receptors, comprising infecting insect host cells with: (a) a recombinant baculovirus comprising DNA encoding human interleukin 5 receptor α-chain and a second recombinant baculovirus comprising DNA encoding human interleukin 5 receptor β-chain or (b) a recombinant baculovirus comprising DNA encoding both human interleukin 5 receptor α-chain and β-chain, to produce an infected host cell coexpressing said DNA encoding human interleukin 5 receptor α-chain and human interleukin 5 receptor β-chain, and maintaining the infected host cells under conditions permitting the coexpression of said DNA encoding human interleukin 5 receptor α-chain and human interleukin 5 receptor β-chain.

7. The method of claim 6 wherein cells that express high affinity human interleukin 5 receptors are frozen.

8. The method of claim 6 wherein said host cell is infected with a first recombinant baculovirus comprising DNA encoding human interleukin 5 receptor α-chain and a second recombinant baculovirus comprising DNA encoding human interleukin 5 receptor β-chain.

9. The method of claim 6 wherein said host cell is infected with a recombinant baculovirus comprising DNA encoding both human interleukin 5 receptor α-chain and DNA encoding human interleukin 5 receptor β-chain.

\* \* \* \* \*

UNITED STATES PATENT AND TRADEMARK OFFICE
CERTIFICATE OF CORRECTION

PATENT NO : 5,861,279
DATED : January 19, 1999
INVENTOR(S) : Ji Zhang, Peng Wang It is certified that error appears in the above-identified patent and that said Letters Patent is hereby corrected as shown below:

On the title page, item [22] Filed: should read -- Jan. 17, 1997 --

Signed and Sealed this

Twenty-fifth Day of May, 1999

Attest:

Q. TODD DICKINSON

*Attesting Officer*    *Acting Commissioner of Patents and Trademarks*

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( x i ) SEQUENCE DESCRIPTION: SEQ ID NO: 1:

TTTACTGTTT TCGTAACAGT TTTG        24

( 2 ) INFORMATION FOR SEQ ID NO: 2:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( x i ) SEQUENCE DESCRIPTION: SEQ ID NO: 2:

CAACAACGCA CAGAATCTAG        20

( 2 ) INFORMATION FOR SEQ ID NO: 3:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( x i ) SEQUENCE DESCRIPTION: SEQ ID NO: 3:

AAGCAAATGT GTAACCATCC TCCACAAAGG        30

( 2 ) INFORMATION FOR SEQ ID NO: 4:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( x i ) SEQUENCE DESCRIPTION: SEQ ID NO: 4:

AAAGCAATGG ATTGGAAAAG CAGACACTGG        30

( 2 ) INFORMATION FOR SEQ ID NO: 5:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( x i ) SEQUENCE DESCRIPTION: SEQ ID NO: 5:

```
AAGGACAGCA  AGACCGAGAC  C                                                    2 1
```

( 2 ) INFORMATION FOR SEQ ID NO: 6:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( x i ) SEQUENCE DESCRIPTION: SEQ ID NO: 6:

```
CCCCCAGCAG  GCAGACACAG  G                                                    2 1
```